United States Patent [19]
Prywes

[11] Patent Number: 6,007,511
[45] Date of Patent: Dec. 28, 1999

[54] SHUNT VALVE AND THERAPEUTIC DELIVERY SYSTEM FOR TREATMENT OF GLAUCOMA AND METHODS AND APPARATUS FOR ITS INSTALLATION

[76] Inventor: Arnold S. Prywes, 12 Jason Ct., Dix Hills, N.Y. 11746

[21] Appl. No.: 07/696,859

[22] Filed: May 8, 1991

[51] Int. Cl.$^6$ .................................................. A61M 5/00
[52] U.S. Cl. ............................................. 604/9; 606/108
[58] Field of Search ..................... 623/4, 6; 606/107, 606/108; 604/8–10, 294, 264

[56] References Cited

U.S. PATENT DOCUMENTS

| | | | |
|---|---|---|---|
| 3,960,150 | 6/1976 | Hussain et al. | 604/294 |
| 4,722,724 | 2/1988 | Schocket | 604/8 |
| 4,750,901 | 6/1988 | Molteno | 604/8 |
| 4,787,885 | 11/1988 | Binder | 604/8 |
| 4,826,478 | 5/1989 | Schocket | 604/8 |
| 4,902,292 | 2/1990 | Joseph | 623/4 |
| 4,911,161 | 3/1990 | Schechter | 606/171 |
| 4,915,684 | 4/1990 | Mackeen et al. | 604/8 |
| 4,936,825 | 6/1990 | Ungerleider | 604/8 |
| 4,946,436 | 8/1990 | Smith | 604/8 |
| 4,968,296 | 11/1990 | Ritch et al. | 604/8 |
| 5,041,081 | 8/1991 | Odrich | 623/4 |
| 5,057,098 | 10/1991 | Zelman | 606/107 |
| 5,071,408 | 12/1991 | Ahmed | 606/108 |
| 5,092,837 | 3/1992 | Ritch et al. | 604/8 |

*Primary Examiner*—Mark Bockelman
*Attorney, Agent, or Firm*—Ladas & Parry

[57] ABSTRACT

A shunt valve for treatment of glaucoma in the form of a hollow tubular body insertable into a hole formed in the sclera and provided with retaining shoulders that hold the tubular body in place against fore and aft movement. The valve is carried on and transported by a tool at the front end of which projects a cutting member. The cutting member is driven from an energy source under the control of an operator to form a hole in the sclera after which the valve is displaced axially from the tool along a straight line into the hole coaxially thereof. A porous inflatable balloon can be carried by the valve or installed therein subsequent to the implantation of the valve in the sclera to control drainage through the valve. Medicaments and the like can be supplied with the inflatable balloon. The cutting member can be a rototrephine or a laser cutter.

54 Claims, 7 Drawing Sheets

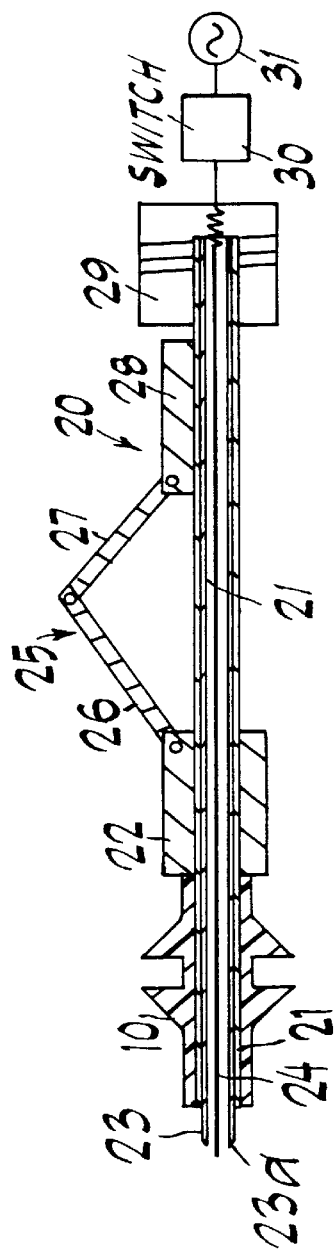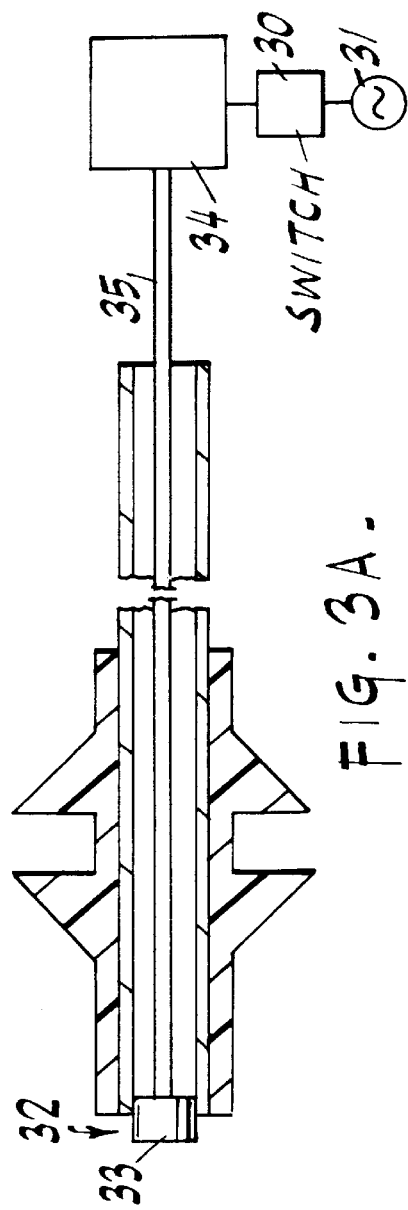
FIG. 3.
FIG. 3A.

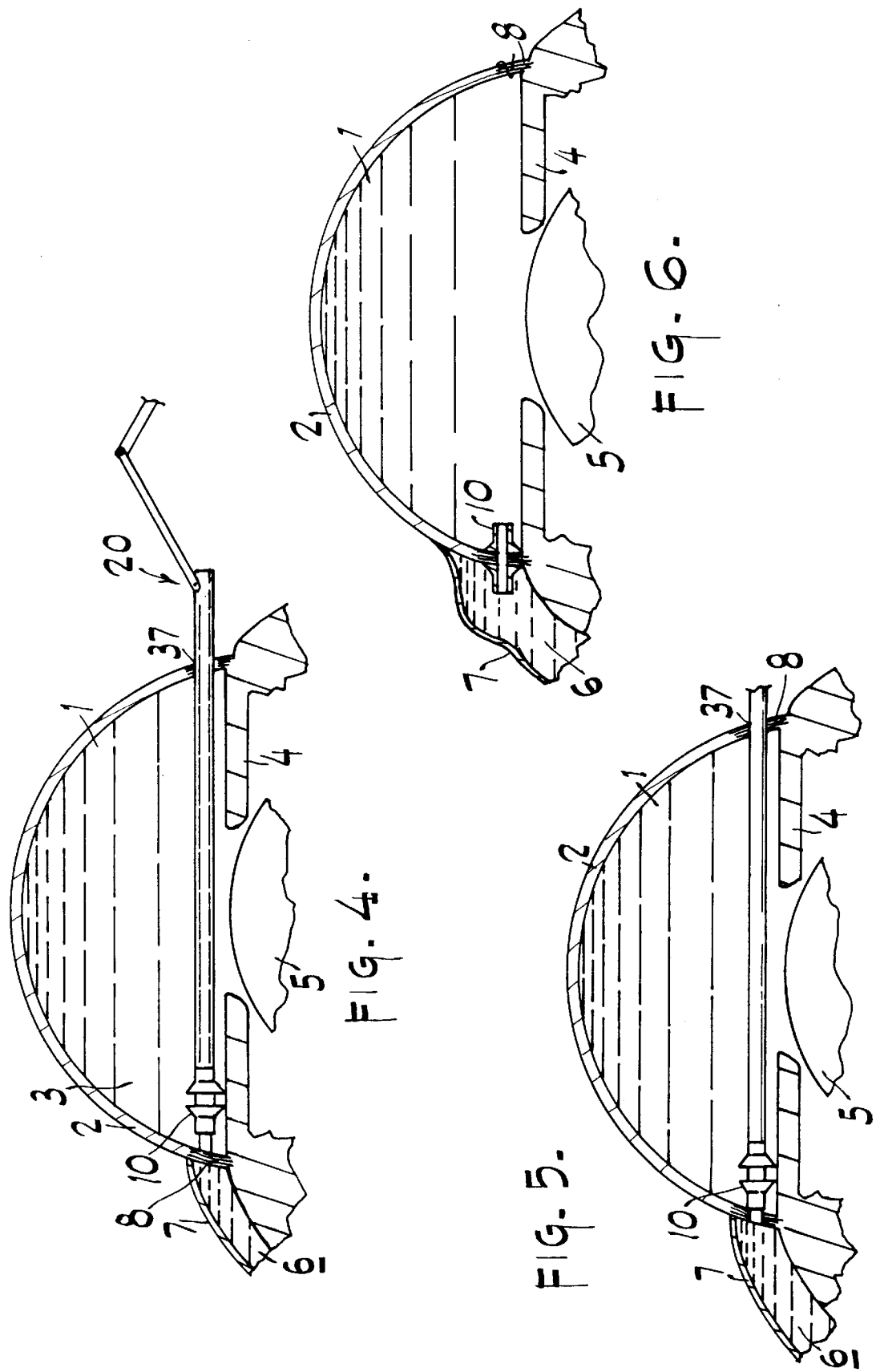

SHUNT VALVE AND THERAPEUTIC DELIVERY SYSTEM FOR TREATMENT OF GLAUCOMA AND METHODS AND APPARATUS FOR ITS INSTALLATION

FIELD OF THE INVENTION

The invention relates to the reduction of elevated pressure in organs of the human body and to delivery of therapeutic drugs to the organs.

The invention relates, in particular, to the treatment of glaucoma and especially to methods and apparatus for the reduction of intraocular pressure in the eye by insertion of a shunt in the eye which provides communication between the anterior chamber and the subconjunctival space. The invention further relates to methods and apparatus associated with the shunt for delivery of therapeutic drugs to the eye.

BACKGROUND AND PRIOR ART

Glaucoma is a general term applicable to diseases of the eye in which the intraocular pressure in the eye increases to a level which can cause damage to the structures within the eye. If the pressure increases suddenly as in acute angle closure glaucoma, surgical intervention is immediately required to reduce the intraocular pressure and prevent permanent damage to the eye structure. When the pressure increase is gradual as in open angle and neovascular glaucoma, one mode of treatment for reducing the pressure involves treatment with medication, for example, by a topical application to the eye and/or by oral administration. In more severe cases when the pressure resists control by medication, more aggressive intervention involves the installation of a shunt valve which connects the anterior chamber to the subconjunctival space. This promotes drainage or the fluid from the anterior chamber so that the pressure in the eye can be relieved.

In one embodiment of a shunt valve, referred to as a standard length "Krupin" glaucoma valve implant, the implant comprises an open plastic tube which is placed into the anterior chamber, an elastic tube fixed to the plastic tube and plastic side arms extending laterally of the plastic tube for fixation of the implant. The elastic tube has a closed distal end with vertical and horizontal slits forming unidirectional and pressure sensitive valve openings. The distant end of the elastic tube remains outside the eye. In order to install the implant it is necessary to make an external conjunctival incision and to form scleral and conjunctival flaps. The implant is placed in the bed of the scleral flap. The plastic tube must be cut to length during surgery so that the open end of the plastic tube will not contact the iris or cornea. The implant is sutured in place using the side arms as anchor points in order to prevent anterior—posterior movement. The scleral flap is closed by suturing and the conjunctiva is also closed by suturing.

In another embodiment, known as the long "Krupin" glaucoma implant, the valve end of the elastic tube is first sutured within the groove of an elastic band and the band is sutured against the sclera. A notch is formed in the elastic band through which the elastic tube extends for connection to the plastic tube. The elastic tube is sutured to the sclera. The elastic band with the elastic tube therein extends beneath both horizontal rectus muscles. As in the first described embodiment, the plastic tube is placed in the scleral bed and penetrates into the anterior chamber. Sutures are necessary to fixate the plastic tube to the sclera and to close the scleral flap and the conjunctiva. The end of the elastic tube with the valve slits remains within the subconjunctival space.

In another embodiment, known as a Molteno implant, an open silicone rubber tube extends 2 to 4 mm into the anterior chamber and the tube is attached to and opens onto the upper surface of a thin acrylic episcleral plate 13 mm in diameter. The edge of the plate has a thickened rim that is perforated to permit attachment of the tube. The plate is sutured to the sclera. As in the other embodiments, scleral and conjunctival flaps are formed. The tube is sutured to the sclera at the posterior edge of the scleral flaps.

All of the above embodiments and variations thereof have numerous disadvantages and relatively low success rates. They all involve substantial trauma to the eye and require great surgical skill. The eye is exposed to long periods of surgery and considerable manipulation of tissue. The implants themselves are complex and require careful installation to prevent leakage, damage to the lens or iris, dissection of muscle tissue as well as blockage of flow through the tube passages. Frequently, it is necessary to perform corrective surgery to overcome complications due to the implant surgery.

SUMMARY OF THE INVENTION

An object of the invention is to provide a shunt of simple construction and a method for its installation in the eye of a patient which is simple, rapid and involves minimal trauma to the eye.

A further object of the invention is to provide a shunt and a method for its installation which will avoid the disadvantages of the known art by eliminating suturing of the implant to fix it in place, avoiding dissecting muscular tissue and minimizing manipulation thereof.

In accordance with a feature of the invention, the installation of the implant takes advantage of the elasticity of the sclera to eliminate the need for sutures. The invention contemplates the formation of a hole in the sclera, and more specifically, the trabecular meshwork thereof, by a cutting tool and insertion of the shunt into the hole for elastic retention therein.

According to the invention, a tool or instrument for installation of the implant has a cutting means to form a hole in the sclera, and a hollow shunt is carried by the tool and after the hole is formed in the sclera, the hollow shunt is inserted into the formed hole to provide communication between the anterior chamber on one side of the sclera and the subconjunctival space on the other side of the sclera. Thereby, pressure in the anterior chamber is relieved by drainage of the aqueous humor from the anterior chamber into the subconjunctival space.

A feature of the invention is that the procedure can be carried out in a single stage of placing the tool and forming the hole and inserting the shunt into the formed hole. Hence, the tool serves the functions of transporting the shunt to a position for its installation into the sclera, forming the hole in the sclera, and guiding the shunt for insertion into the hole in the sclera.

Although the invention will be described with reference to the installation of a shunt into the sclera between the anterior chamber and the subconjunctival space of the eye, it is equally applicable to the formation of a hole in any elastic membrane in the body of a patient separating a high pressure chamber and a low pressure chamber, for example, the bladder, the ureter, urethra, bile duct, etc.

Accordingly, according to a broad aspect of the invention, it is applicable to the combination of a means for forming a hole in any elastic membrane in the body of a patient separating a high pressure chamber and a low pressure chamber and hollow shunt means carried by the hole forming means for being transported therewith and for being inserted into the hole and elastically engaged with the elastic membrane to establish communication between the high pressure chamber and the low pressure chamber.

In further accordance with the invention, the hollow shunt means can carry means for controlling flow of fluid through the shunt means from the high pressure chamber to the low pressure chamber. The latter means can be an inflatable member in the form of a balloon. The inflatable member is coupled to the shunt means for controlling communication between the shunt means and the high pressure chamber and for this purpose the inflatable member is porous.

The means for controlling the flow of fluid through the shunt means can be in the form of a separate module which is inserted into the shunt means, for example, after the shunt means has been elastically engaged with the elastic membrane. Alternatively, the means for controlling the flow of fluid through the shunt means can be integral with the shunt means and be activated after the shunt means has been implanted.

In further accordance with the invention, a therapeutic agent can be associated with the inflatable member to release the therapeutic agent into the low pressure chamber when the inflatable member is inflated.

In one embodiment of the shunt means according to the invention, it is constructed as a tubular body dimensioned to engage the sclera for being retained thereby, the tubular body having opposed retaining shoulders which engage the sclera on opposite sides thereof.

In one embodiment, the means for forming the hole in the sclera comprises a tubular cutting member having a cutting end for forming the hole in the sclera and the tubular body of the shunt is slidably engaged with the tubular cutting member. The tubular cutting member carries means operable from outside the eye for displacing the tubular body of the shunt from the cutting member to insert the tubular body into the hole formed in the sclera.

The tubular cutting member is operated from an energy source under the control of an operator from outside the eye. Hence, when the cutting member is a rotary cutting means, such as a trephine, the operator controls connection of the trephine with a drive motor by a foot-operated switch whereas when the cutting member is a laser cutter, the operator connects the energizing source to the laser cutter by a foot-operated switch.

The tubular body of the shunt can be constructed with conical portions whose larger ends form the shoulders and these define an annular slot, for example, of ovoid shape which is dimensioned to receive the region of the sclera surrounding the hole when the tubular body is installed therein. The shoulders can also be formed by fin-like extensions attached to the tubular hollow body which can be placed externally on or internally within the cutting inserting instrument.

A significant aspect of the invention is the method of installing the shunt, and in this regard it is advantageous to form the hole in the sclera in the direction from the anterior chamber to the subconjunctival space. To achieve this, an incision is first formed in the cornea at a distance from the location where the hole is to be formed in the sclera and then the hole forming tool is progressively inserted through the anterior chamber towards the trabecular meshwork. Thereafter, the hole forming tool produces the hole in the sclera (trabecular meshwork) and the hollow shunt is inserted into the hole in the direction from the anterior chamber to the subconjunctival space. The shunt is displaced from the tool in a straight line axially of the tool and coaxially of the hole. The straight line displacement and installation of the shunt simplifies and minimizes the travel of the shunt, thus insuring its correct placement in the hole in the sclera.

After implantation of the shunt in the hole in the sclera, the hole forming tool is removed through the initial incision in the cornea and a suture is placed thereat. As the only suturing involved in the entire operation is remote from the installation of the shunt, it has virtually no effect on the installation. The tool is displaced in the anterior chamber both during insertion and removal approximately parallel to the iris and the lens.

Among the advantages of the method and construction of the shunt are that the method of insertion is substantially simplified when compared to the prior art as no sutures are required to anchor the implant. Furthermore, there is minimized trauma and scarring. A further advantage of the invention is the utilization of the same instrument which forms the hole to carry the implant and enable its emplacement. This leads to simple surgery with less likelihood of failure due to its less invasive nature. The possibility of modularity which allows revision of the simple shunt, and the use of therapeutic agents within the uninflated balloon nodule make the surgery more likely to be successful.

BRIEF DESCRIPTION OF THE FIGURES OF THE DRAWING

FIG. 3 is a side elevational view of an instrument for installing the shunt in which the shunt is mounted on the instrument.

FIG. 3A is a partial sectional view of a modified instrument utilizing a laser cutter.

FIG. 4 is a diagrammatic sectional view through an eye showing a first position of the instrument and shunt in an operation for installation of the shunt.

FIG. 5 is similar to FIG. 4 and shows a second stage of the operation in which the hole is formed in the sclera and the shunt is ready for installation into the hole.

FIG. 6 is similar to FIG. 5 and shows a third stage of the operation in which the instrument has been retracted from the eye and the shunt valve is in place.

DETAILED DESCRIPTION OF PREFERRED EMBODIMENTS OF THE INVENTION

Figure 1A:
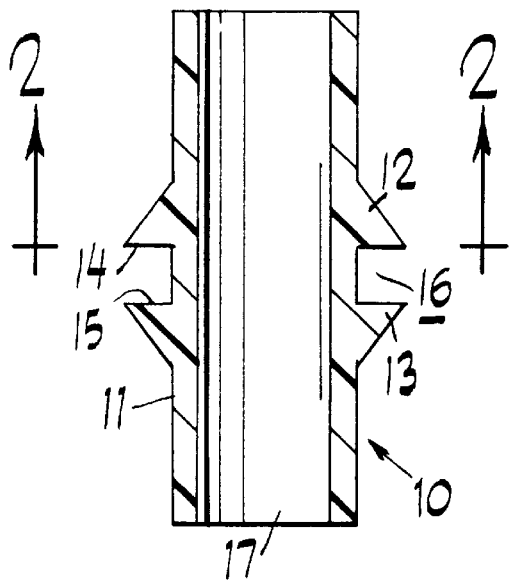
FIG. 1A is an enlarged side elevation view of one embodiment of a shunt according to the invention.

Referring to FIG. 6, therein is shown a simplified and diagrammatic illustration of the eye structure in the minimum detail to illustrate the invention in a clear fashion. The anterior aspect of the anterior chamber 1 of the eye is the cornea 2 whereas the posterior aspect is the iris 4 beneath which is the lens 5. The anterior chamber 1 is filled with aqueous humor 3. The aqueous humor 3 drains into the subconjunctival space 6 through the trabecular meshwork (not shown in detail) of the sclera 8. The aqueous humor is drained from the subconjunctival space 6 through a venous drainage system (not shown). The subconjunctival space 6 is formed between the conjunctiva 7 and the sclera 8.

In conditions of glaucoma, the pressure of the aqueous humor in the eye (anterior chamber) increases and this resultant increase of pressure can cause damage to the vascular system at the back of the eye and especially to the optic nerve. The treatment of primary glaucomas, and other diseases which lead to elevated pressure in the anterior chamber (secondary glaucomas), involves relieving pressure to a normal level.

Figure 1B:
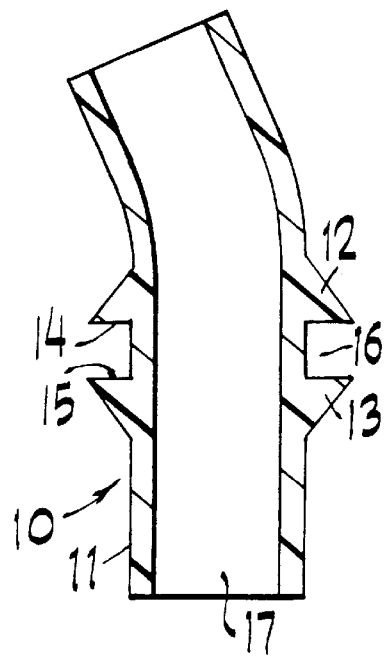
FIG. 1B is an elevational view of the shunt in FIG. 1A turned 90°.
Figure 2A:
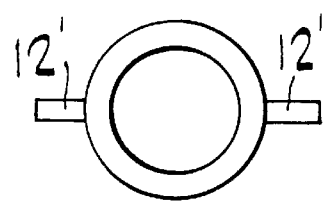
FIG. 2A is a sectional view similar to FIG. 2 showing a modified version of the shunt.
Figure 2:
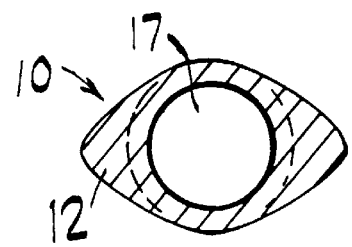
FIG. 2 is a sectional view taken along line 2—2 in FIG. 1A.
Figure 7:
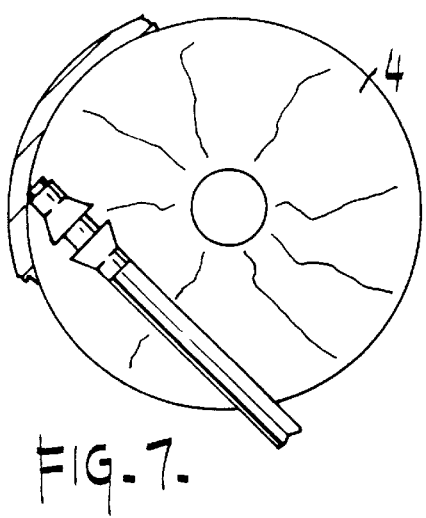
FIG. 7 is a top plan view of the position shown in FIG. 4.
Figure 8:
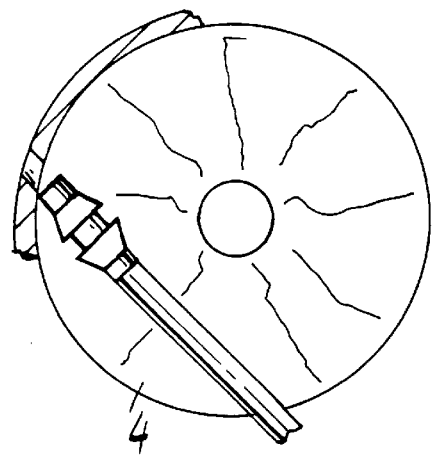
FIG. 8 is a top plan view of the position shown in FIG. 5.
Figure 9:
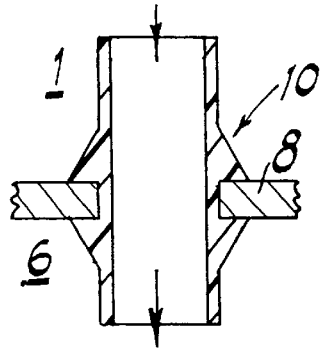
FIG. 9 is a sectional view on enlarged scale showing the shunt installed in the sclera.

FIGS. 1A, 1B and 2 illustrate one embodiment of a shunt valve 10 of the invention which is intended to relieve the intraocular pressure in the anterior chamber by providing a flow path from the anterior chamber 1 to the subconjunctival space 6. The shunt valve 10 conprises a tubular body 11 having an outer surface on which are formed opposed conical portions 12 and 13 of opposite conicity. The larger diameter ends 14 and 15 respectively of conical portions 12 and 13 form shoulders which face one another in spaced relation to define a slot 16 therebetween. The cross section of the conical portions 12 and 13 can be of any rounded shape but they are substantially elliptical or ovoid in this embodiment as shown in FIG. 2. The slot 16 formed between opposed shoulders 14 and 15 is dimensioned to engage the sclera 8 in an installed position as shown in FIG. 6. The valve 10 has an axial bore 17 extending completely therethrough to establish communication between the anterior chamber 1 and the subconjunctival space 6 as shown in FIGS. 6 and 9. The direction of flow of the aqueous humor is shown by the arrows in FIG. 9.

The shunt valve 10 can be made of a conventional plastic material such as polymethyl methacrylate, silicone or the like.

The valve can also be made of a hydrophilic substance which will swell upon contact with the aqueous humor. Known hydrogels serve this function. The valve can also be made of a material which slowly dissolves in the aqueous humor, such as collagens, and they can contain medications such as anti-inflammatory, thrombotic, anti-scarring, or anti-cross-linking agents.

The thickness of slot 16 is about 0.7 mm which will enable the valve 10 to engage the sclera 8 to be maintained thereby in a secure position against fore and aft movement so that the open ends of the tubular body will respectively communicate with the anterior chamber 1 and the subconjunctival space 6 for allowing flow of aqueous fluid from the anterior chamber to the subconjunrctival space.

Figure 9A:
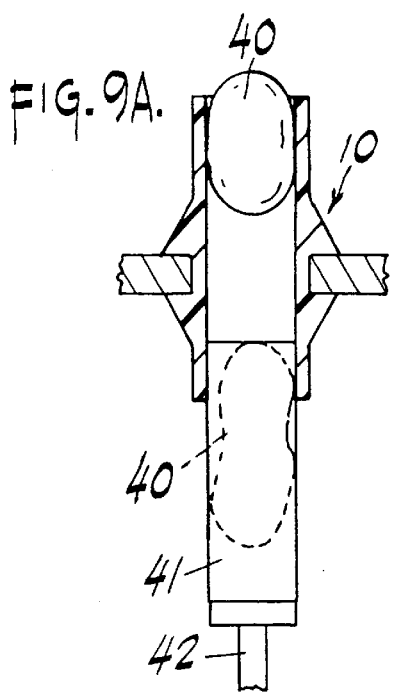
FIG. 9A shows a modification of the shunt in FIG. 9 in which a medication plug is utilized.

In a particular embodiment, the tubular body 11 has an outer diameter of about 2 mm and the thickness of the tubular body is about 0.25 mm. The larger diameter of the elliptically shaped conical portion at shoulders 14 and 15 is about 3 mm and the smaller diameter is about 2.5 mm. The overall length of the valve is about 5.7 mm and each conical portion has a length of about 0.5 mm. Although the tubular body 11 has been shown as having portions of equal length forward and rearward of conical portions 12 and 13, the portion rearward of conical portion 13, i.e. the anterior portion, can be foreshortened, for example, as shown in FIGS. 9 and 9A. This will make it less likely to strike the iris or lens.

In FIG. 1B it is seen that the upper half of the valve shunt is curved to conform to the curvature of the globe of the eye.

Figure 17:
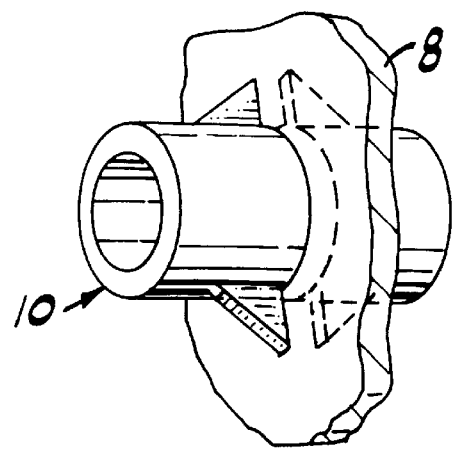
FIG. 17 is a diagrammatic illustration of the embodiment in FIG. 16 installed in the sclera.
Figure 18:
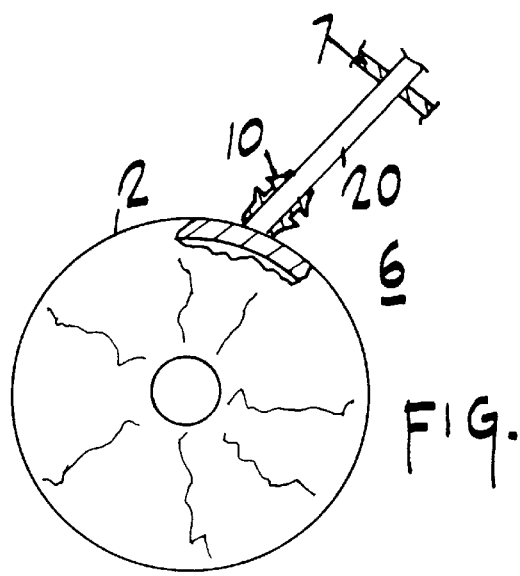
FIG. 18 is a plan view showing another embodiment of the method of the invention in which the shunt is prepared for insertion into the sclera from outside the eye through the subconjunctival space.
Figure 19:
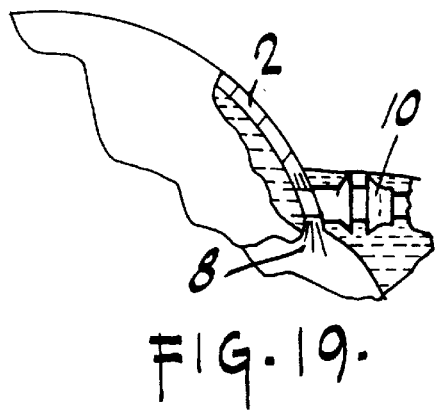
FIG. 19 is a side view of the arrangement in FIG. 18.
Figure 20:
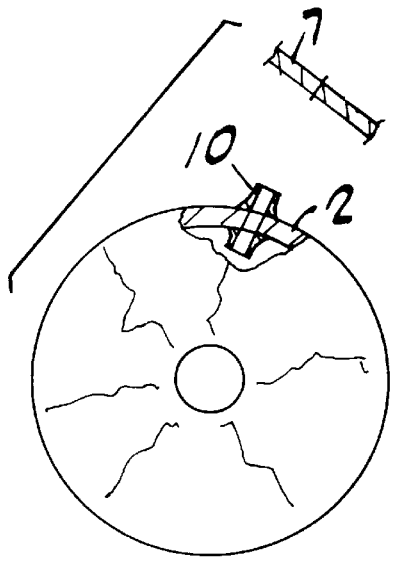
FIG. 20 is a plan view showing the shunt in FIG. 18 in installed state.
Figure 21:
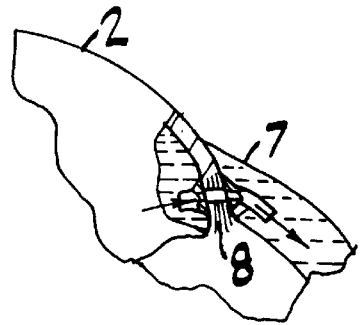
FIG. 21 is a side view of the arrangement in FIG. 20.

FIGS. 2A and 17 show a modified version of the shunt valve in which instead of conical portions, the valve is provided with flexible triangular fins or ribs 12' in diametric opposition to one another in respective pairs 82 and 83.

The composition of the material of the valve and its dimensions provide a certain amount of flexibility for the valve allowing it to deform elastically from the configuration illustrated in FIGS. 1A and 1B and to return to its initial position after such elastic deformation. This is significant in the installation of the valve as will be explained later.

The invention will now be described with reference to one method of installation of the valve and to a tool or instrument which is operated in combination with the valve for its installation in the sclera.

Referring to FIGS. 3 and 4, therein is seen a tool or instrument 20 which enables the installation of the valve 10 in the sclera. The instrument 20 comprises a tubular casing 21 on the end of which the valve 10 can be slidably engaged with slight frictional fit in order to be retained thereat. The valve 10 abuts at one end thereof against a sleeve 22 which is slidably mounted on the casing 21. Rotatably supported within the casing 21 is a cutting means 23 in the form of a rototrephine having a cutting tip 23a projecting beyond the end of the casing 21. Centrally mounted in a fixed position within the cutting means 23 is a cauterizing or diathermy rod 24 whose tip extends slightly beyond the tip 23a of cutting means 23. A linkage 25 is connected to sleeve 22 to displace the sleeve longitudinally on the casing in order to slide the valve 10 off the casing 21. The linkage 25 comprises a link 26 hinged to the sleeve 22 and a link 27 hinged to link 26 and hinged to a fixed sleeve 28 on the casing 21. The linkage 25 initially has a folded configuration as shown in FIG. 3 so that if the link 27 is manually depressed by pivoting link 27 around the hinged connection with sleeve 28, the sleeve 22 will be displaced on the casing 21 and apply force to the end of the valve 10 in order to push the valve off the casing 21. As previously explained, the valve 10 initially has a curved (or angulated) shape as shown in FIG. 1B to accommodate itself to the globe of the eye, however, the valve 10 has sufficient flexibility to be mounted in elastically deformed condition on the casing 21 and after the valve has been pushed off the casing 21 it will revert to its original shape as shown in FIG. 1B.

A drive motor 29 is secured to the casing 21 and is operatively connected to the cutting means 23 in order to produce rotation thereof. The motor 29 and the diathermy rod 24 are connected through a foot controlled switch 30 to an electrical power supply 31. The motor 29 can be separated from the instrument and connected to the cutting means 23 by a flexible drive shaft in order to make the instrument lighter and more compact. In this regard, the diathermy rod 24 can be omitted and made integral with the tip 23a of the cutting means 23. In such case, a coating is provided on the outer surface of casing 21 to prevent heat-conduction to valve 10 of the diathermy energy. FIG. 3A shows a modified embodiment of the tool in which the rototrephine is replaced by a laser cutting means 32. In this embodiment the diathermy rod is omitted entirely. The laser cutting means 32 comprises a laser tip probe 33 which extends slightly beyond the casing 21 and a laser generator 34 which activates the probe 33 when connected by switch 21 to power supply 31. When probe 33 is activated, it produces a laser cutting beam which can form the desired hole in the sclera. The laser energy produced by laser generator 34 is transmitted to the probe 33 by a fiber optic sleeve 35 in casing 21.

A feature of the method of installation of the valve is that the valve is engaged with the sclera in the direction from within the anterior chamber 1 to the subconjunctival space 6, the entry site of the valve and tool being made at a location remote from the site at which the valve is implanted in the sclera. Specifically, with reference to FIG. 4, the entry site is shown at 37 where a small incision is made in the cornea to permit insertion of the valve and the instrument into the interior of the anterior chamber. Installation of the valve into the sclera therefore, takes place from within the eye. Prior to insertion of the valve and instrument into the anterior chamber, a viscoelastic fluid is injected into the anterior chamber to prevent collapse of the anterior chamber. A saline solution is injected into the subconjunctival space 6 to inflate the space and form a "bleb". The instrument 20 with the valve 10 externally mounted on its end is then inserted, valve-first, through the incision 37. The instrument is inserted substantially parallel to the iris to avoid contact with the corneal endothelium. When the instrument is located in the position shown in FIG. 4. the operator activates the cutting means 23 and the diathermy rod 24. The tool can then be advanced to form a hole 38 in the sclera and to position the end of the valve 10 at the inner surface of the sclera where the hole has been formed. A suction device can be attached to the tool to produce suction within the casing 21 in order to withdraw any trephined tissue produced by the cutting means 23. Such suction device is not necessary with the laser cutter as no superfluous matter is produced. By actuating the link 27 from outside the eye, the sleeve 22 will be longitudinally advanced on the casing 21 to push the valve 10 into the formed hole 38 in the sclera. The lumen of the sclera has sufficient flexibility to allow the valve to penetrate into the hole 38 formed in the sclera and when the valve has been advanced a sufficient distance, the sclera will elastically engage in the slot 16 in the valve so that elastically engage in the slot 16 in the valve so that the valve will be elastically retained by the sclera with the shoulders 14 and 15 blocking fore and aft movement of the valve. The movement of the valve from the instrument into the hole 38 in the sclera takes place over a short distance and the valve moves in a straight line axially on the tool and coaxially into the formed hole. The tapered shape of the conical portion 12 or the fin 12' facilitates entry of the valve into the formed hole. The casing 21 remains in the formed hole as the valve is inserted and serves as a guide and a stint. When the valve 10 has been implanted in the sclera, the instrument is withdrawn from the valve and removed through the incision 37. Under some circumstances, the casing 21 can be retracted slightly to be withdrawn from the hole 38 in the sclera and the valve can be inserted into the empty hole.

After the valve has been implanted and the instrument has been removed, a suture 39 is placed on the incision 37 to close the same. Inasmuch as the incision 37 is distant from the implant site and from the sclerectomy, there is minimum trauma to the eye at the implant site.

When the valve is in position in the hole in the sclera, it establishes communication between the anterior chamber 1 and the subconjunctival space 6 so that aqueous fluid is free to drain from the anterior chamber into the subconjunctival space and thereby reduce the intraocular pressure.

FIG. 9A shows a modification in which a plug 40 is inserted into the implanted valve 10. The plug 40 can serve to control the rate of egress of fluid from the anterior chamber 1 while delivering medication agents which can prevent scarring and closure of the valve. The plug 40 may be dissolvable in the aqueous fluid over a period of time and thus prevent early excessive fluid runoff and secondary loss of anterior chamber depth. The dissolving material of the plug 40 can contain anti-inflammatory, anti-scarring, anti-thrombotic or anti-cross-linking agents. The plug 40 can also be made of a hydrophilic substance which swells when in contact with aqueous fluid. The plug 40 can also be made porous to allow fluid flow therethrough while delivering dissolvable medication to the eye.

The plug 40 can be installed in the valve 10 after the valve has been implanted in the sclera by inserting a tube 41 through the incision 37 into the implanted valve 10. The plug 40 is carried by the tube 41. Within the tube is mounted a plunger 42 which is controlled from outside the eye and when the tube 41 has been inserted into the valve 10, the plunger 42 is advanced to push the plug 40 out of the tube 41 into the implanted valve 10.

Figure 10:
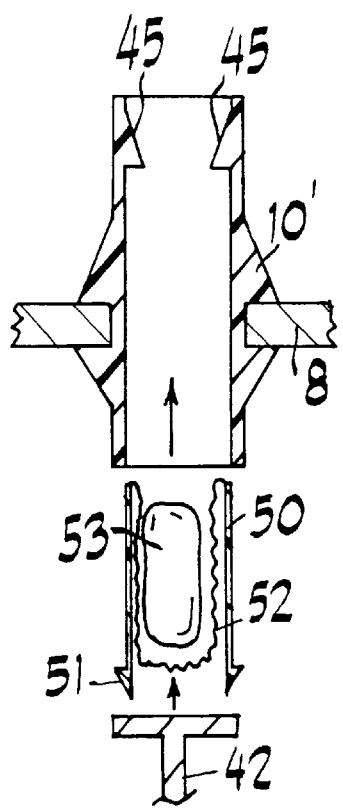
FIG. 10 shows a modified embodiment of the shunt employing a module for fluid flow control and for dispensing medication.
Figure 12:
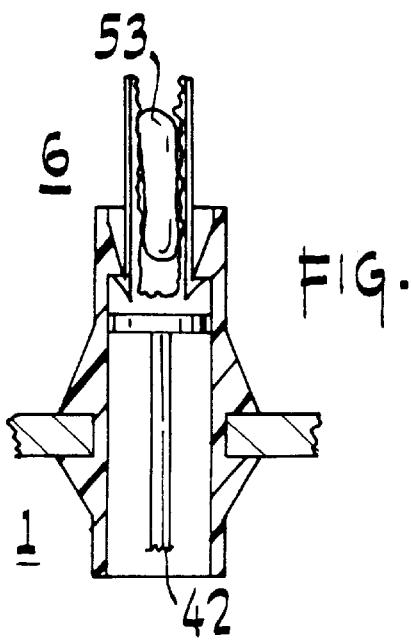
FIG. 12 shows a module engaged with the shunt.

FIG. 10 shows a modified embodiment of the valve at 10' and this embodiment provides internal tapered ribs 45 at the inner surface of the forward end of valve 10'. In FIG. 10, a module 50 is inserted into the interior of the valve 10' after the latter is implanted in the sclera. In this arrangement, the module 50 is slidably carried within tube 41 (not shown in FIG. 10) which is inserted into the rear portion of the implanted valve 10'. Thereafter, plunger 42 is advanced to displace the module 50 from the tube 41 until external stops 51 on the module 50 engage internal ribs 45 on the valve 10' as illustrated in FIG. 12. In this position, the module 50 will extend into the subconjunctival space 6. The module 50 contains an inflatable member 52 which is initially retracted and uninflated within the interior of the module 50. The inflatable member 52, in turn, contains a plug 53 which can be of the same composition of plug 40 described with reference to FIG. 9A. The inflatable member 52 is in the form of a pancake-shaped balloon with variable permeability micropores. The balloon can be inflated by introducing a pressure fluid through the tube 41 after retraction of the plunger 42. When the balloon is inflated, it will occupy subconjunctival space and control the rate of drainage of the fluid from the anterior chamber into the subconjunctival space. Concurrently, the medication agents carried in the plug 53 will be delivered into the subconjunctival space. The balloon is seen in plan view in inflated state in FIG. 14 and in elevation in FIG. 15. The diameter of the inflated balloon is 5 mm or more and its flatter cross-section elevates the subconjunctival space only about 2 to 3 mm. This minimizes discomfort of the lid of the patient moving across a "lump" rather than a flatter surface.

Figure 15:
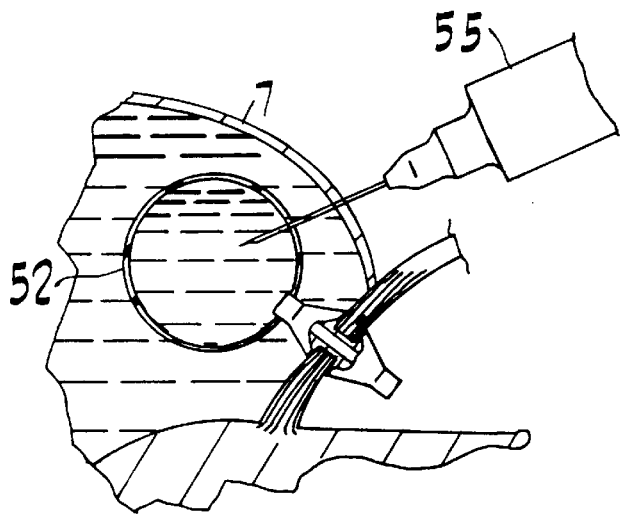
FIG. 15 diagrammatically illustrates external introduction of medicament into the inflatable member of the module.

As shown in FIG. 15 the balloon can be filled with a therapeutic agent by injection directly into the balloon by a needle syringe 55 through the conjunctiva 7. The therapeutic agent can be an anti-inflammatory, anti-glaucoma, antibacterial, anti-thrombotic or anti-fungal agent or the like. Anti-cancer medications can also be supplied to the balloon. The balloon allows gradual release of the medication into the eye. The balloon 52 can be composed of a self-sealing material to prevent rapid egress of injected medicine through the puncture site of the needle syringe.

Figure 11:
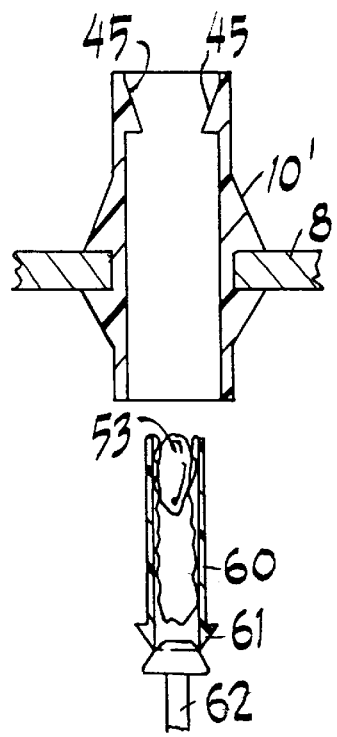
FIG. 11 shows the shunt of FIG. 10 installed in the sclera and ready to receive the module.
Figure 11A:
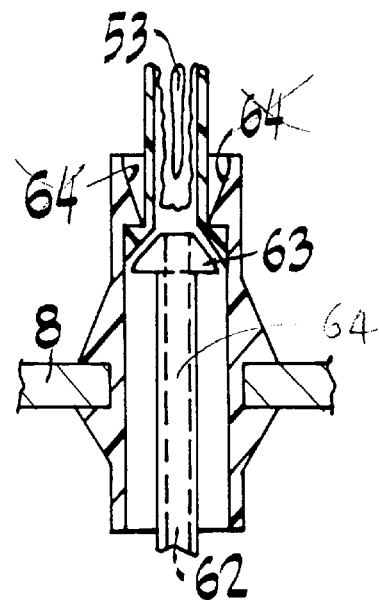
FIG. 11A shows the nodule installed in the shunt.

FIGS. 11 and 11A show a variation of the embodiment in FIGS. 10 and 12 and in FIGS. 11 and 11A the valve 10' corresponds to that in FIGS. 10 and 12. In FIGS. 11 and 11A, the module 60 is distinguished from the module 50 in that module 60 has internal stops 61 rather than the external stops 51 shown in FIG. 10. In FIGS. 11 and 11A, the plunger 62 serves to displace the stops 61 laterally so that the stops 61 can engage the internal ribs 45 on the valve 10' when the module 60 has been displaced into the valve. For this purpose, the plunger 62 has a conical head 63 so that when the plunger is axially displaced, the head 63 will cause the stops 61 to flare outwardly around thin weakness zones 61a in the wall of module 60 and occupy a permanent outwardly displaced position. In the outwardly displaced position, the stops 63 engage the ribs 45 to limit the displacement of the module 60 within the valve.

The plunger 62 is provided with a longitudinal bore 64 extending therethrough for passage of a pressure fluid to inflate the member 52 into the subconjunctival space 6 and to expel the medicine plug 53 into space 6. When the balloon is inflated, it is held in the subconjunctival space, by the tissue thereof to anchor the module in the valve.

Figure 13:
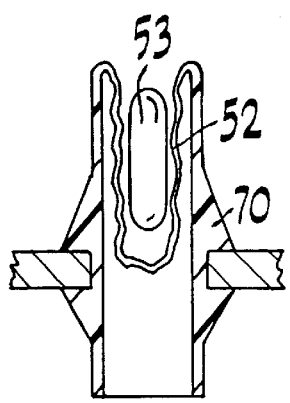
FIG. 13 shows a modified embodiment of the shunt in which the module is integral therewith.
Figure 14:
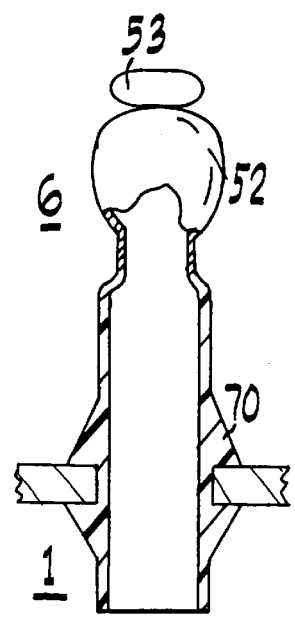
FIG. 14 shows an inflated member of the module.

Instead of inserting a separate module into the valve as shown in FIGS. 10–12, the valve can be constructed according to the modification shown in FIGS. 13 and 14 as a one-piece valve 70 at the front end of which an inflatable member 52 is secured and a plug of medicine 53 is contained within the collapsed and retracted inflatable member 52.

The installation of the valve 70 is carried out as described previously except in two steps. In the first step, the hole is formed in the sclera by the cutting means of the tool, whereafter the tool is withdrawn, the valve 70 is placed on the tip of the tool and the tool is then reinserted so that the valve 70 can be inserted into the hole formed in the sclera. After the valve is inserted in the sclera, a pressure medium is supplied to the interior of the valve to inflate member 52 into the subconjunctival space 6 as shown in FIG. 14 and to eject the plug 53 into the subconjunctival space 6.

Figure 16:
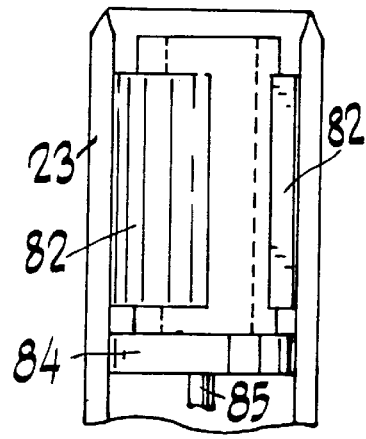
FIG. 16 illustrates another embodiment of the shunt in retracted position within the instrument.
Figure 16A:
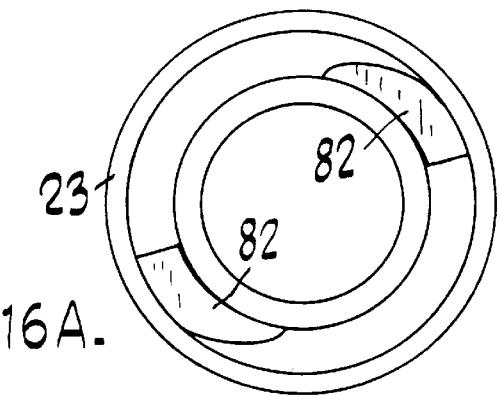
FIG. 16A is a transverse section through the embodiment in FIG. 16.

FIGS. 16, 16A and 17 show a modified valve which is mounted within the cutting tool 23 rather than on the outside casing 21 as shown in the embodiment of FIG. 3. The valve 80 includes a tubular body 81 to which are connected upper and lower pairs 82 and 83 of diametrically opposed triangular fins 12'. In the state as shown in FIGS. 16 and 16A the fins 12' are elastically deformed or folded against the tubular body so that the valve 80 can be contained within the cutting member 23 in a folded inoperative state. After the hole in the sclera has been formed, a plunger 84 mounted within the cutting member 23 (rather than outside the casing 21 as in the embodiment in FIG. 3), is displaced longitudinally to eject the valve 80 from within the cutting member into the hole formed in the sclera. When the fins of pair 82 are displaced from within the cutting member 23, they unfold outwardly under the elasticity of the material of the valve 80 to engage the sclera on the surface thereof facing the subconjunctival space 6. When the cutting tool 23 is withdrawn from the valve 80, the lower pair of fins 83 will unfold and engage the sclera on the surface thereof facing the anterior chamber 1. In FIG. 16, the diathermy rod 24 is not shown but it can extend through the valve 80 and through an axial hole 85 in the plunger 84 or it can be made integral with the cutting member 23. Alternatively, the diathermy rod can be made integral with the cutting tool member. If an inflatable member and/or medication plug is to be employed, this can be installed in the same manner as described with reference to FIGS. 9A and 10–14. In this embodiment it is the facing surfaces of the unfolded fins 82 and 83 which engage the sclera 2 on opposite surfaces thereof to retain the valve 80 in implanted position.

Although the invention has been described with reference to the preferred method of installation of the shunt valve in the direction from the anterior chamber to the subconjunctival space, it is also possible to implant the valve in the sclera working from outside the eye through the subconjunctival space into the anterior chamber. In this variation of the invention as shown in FIGS. 18–21, an initial incision 90 is made in the conjunctiva 7 at a location distant from the implant site of the valve, and the instrument 20 with the valve 10 thereon is introduced through the incision 90 to bring the end of the tool into proximity with the sclera 8 at the location where the hole is to be formed. The drive motor nay be distal to the inserting instrument, and connected to it by a flexible drive shaft. Instead of a diathermy rod, a small diathermy element may be integral with the tip of the cutting means 23. A coating is then provided on the outer surface of the casing 21 to prevent conduction to the valve of the diathermy energy. Alternatively, a laser beam could be used to form the hole by utilizing a fiber optic sleeve in the casing or by forming the inner lumen of the casing as a fiber optic sleeve by suitable coating means. As in the previously described embodiments, the valve may be placed within or on the cutting tool which may be a rototrephine or a laser. The valve 10 will be placed on or in the instrument 20 in a reversed position from that shown in FIG. 3 in order for the valve to be implanted in the sclera in the same configuration as illustrated in FIG. 6. As in the earlier embodiment, the instrument forms the hole in the sclera whereafter the valve is inserted into the formed hole and engaged with the sclera. After the valve has been implanted, the various embodiments of additional plug modules can be employed as previously described with the exception that the plug module will now be installed in the portion of the valve which is disposed in the conjunctival space 6.

A particular feature of the invention is that the valve installation surgery can be carried out simultaneously with cataract and lens implant surgery through a small (3–4 mm.) incision which is currently used for Phakoemulsification surgery with foldable intraocular lens implants.

Another feature of the valve is that it can be placed in an inaccessible part of the subconjunctival space (nasally or inferonasally).

A further feature of the balloon is that it helps to lower introaocular pressure in more than one way. It works as a valve, but it also can work as a drug delivery system with depot medications being able to be injected within the balloon intraoperatively or post operatively. If the shunt becomes occluded, it is possible to re-open the shunt by inserting the module with the balloon. Another use of the balloon is to add long acting pharmacologic agents periodically therein to control intraocular pressure if the valve does not lower intraocular pressure sufficiently. It can be used to release steroids in cases of inflammatory glaucomas, or chemotherapeutic agents for problems such as ocular pemphigoid.

The invention has been described with reference to the eye and particularly to reduction of pressure in the anterior chamber of the eye by increasing drainage to the subconjunctival space 6; however, the invention is applicable, in general, to the reduction of pressure in any high pressure chamber in the body of a patient which is separated from a low pressure chamber by an elastic membrane and to the delivery of medication or therapeutic agents. By way of further example, the invention can be used in the bladder, ureter, gall bladder, or other organs of the body to supply a chemotherapeutic substance to the organ, for example, enzymes could be placed in the balloon to dissolve gall stones, the valve can be used with a pressure sensitive balloon to allow an obstructed bladder to function when there are bladder tumors while delivering a chemotherapeutic agent. The invention is thus addressed to the employment of a hollow shunt which is carried by the hole forming means for being transported therewith and inserted into the bole formed by the hole forming means so as to be elastically engaged with the elastic membrane, and to a drug delivery system associated with the shunt.

By the construction and method of installation according to the invention, the valve is implanted and retained in place without any sutures and with the formation only of a small incision distant from the implant site. This is true whether the valve is installed from within the anterior chamber towards the subconjunctival space or vice-versa. The valve is inserted with the same instrument that forms the hole in the elastic membrane. The valve can be made as one piece and installed in a single step surgical operation or it can be a two-piece unit with a subsequently added module in a two-step operation.

While the invention has been described with reference to preferred embodiments thereof it will be apparent to those skilled in the art that numerous modifications and variations can be made within the scope and spirit of the invention as defined in the attached claims.

What is claimed is:

1. The combination comprising hole forming means for forming a hole in an elastic membrane separating a high pressure chamber and a low pressure chamber in the body of a patient, hollow shunt means removably carried by the hole forming means for being transported therewith and for being inserted into said hole and elastically engaged with said elastic membrane to establish communication between said high pressure chamber and said low pressure chamber, and fluid control means carried by said shunt means for controlling flow of fluid through the shunt means from the high pressure chamber to the low pressure chamber after the shunt means has been inserted into said hole and the hole forming means has been removed from the shunt means.

2. The combination as claimed in claim 1 wherein said means for controlling flow of fluid through the shunt means comprises an inflatable member.

3. The combination as claimed in claim 2 wherein said inflatable member is coupled to said shunt means for controlling communication between said shunt means and said low pressure chamber, said inflatable member being porous.

4. The combination as claimed in claim 3 wherein said inflatable member has variable porosity.

5. The combination as claimed in claim 3 wherein said means for controlling flow of fluid through the shunt means further comprises an inserted module in said shunt means carrying said inflatable member.

6. The combination as claimed in claim 3 wherein said inflatable member is secured to said shunt means and is installed therewith when the shunt means is elastically engaged with said elastic membrane.

7. The combination as claimed in claim 3 comprising means containing a therapeutic agent associated with said inflatable member for release of the therapeutic agent into said low pressure chamber when the inflatable member is inflated.

8. The combination comprising hole forming means for forming a hole in an elastic membrane separating a high pressure chamber and a low pressure chamber in the body of a patient, said hole forming means including an instrument body, an energy source, cutting means on said body operated by said energy source for forming the hole in the membrane, and operator controlled switch means operatively associated with said instrument body for being operated by an operator for selectively connecting and disconnecting said cutting means and said energy source, and hollow shunt means removably carried with the cutting means for being inserted into said hole and elastically engaged with said elastic membrane to establish communication between said high pressure chamber and said low pressure chamber.

9. The combination as claimed in claim 8 for relieving intraocular pressure in an eye of a patient, said high pressure chamber being the anterior chamber of the eye, said low pressure chamber being the subconjunctival space of the eye, and said elastic membrane being the sclera of the eye, said hollow shunt means comprising a tubular body dimensioned to engage the sclera around said hole for retention thereby, said tubular body having one region communicating with said subconjunctival space and a second region communicating with said anterior chamber.

10. The combination as claimed in claim 9 wherein said cutting means comprises a tubular cutting member having a cutting end for forming the hole in the sclera, said tubular body being separably coupled to said tubular cutting member, and means operable from outside the eye for separating said tubular body from said cutting member and inserting the tubular body into the hole formed in the sclera.

11. The combination as claimed in claim 10 wherein said tubular cutting member comprises a rotary cutter.

12. The combination as claimed in claim 10 wherein said tubular cutting member comprises a laser cutter.

13. The combination as claimed in claim 10 wherein said means for separating said tubular body from said cutting member comprises a pusher means coupled to said tubular cutting member for pushing said tubular body away from the tubular cutting member into the hole formed in the sclera.

14. The combination as claimed in claim 13 comprising a cauterizing element in said tubular cutting member having a tip projecting from the cutting end of the tubular cutting member.

15. The combination as claimed in claim 8 wherein said means for forming a hole comprises a tubular cutting means having a longitudinal axis for forming said hole coaxially of said tubular cutting means, and means for displacing said shunt means from said hole forming means along a straight line coaxial with said tubular body for coaxial insertion into said hole.

16. The combination as claimed in claim 9 further comprising means associated with said hollow shunt means for releasing a therapeutic agent into said low pressure chamber.

17. The combination as claimed in claim 16 wherein said means for releasing a therapeutic agent comprises a plug of said therapeutic agent carried by said hollow shunt means in communication with said low pressure chamber.

18. The combination as claimed in claim 16 wherein said means for releasing a therapeutic agent comprises a module coupled to said hollow shunt means and a plug of said therapeutic agent carried by said module in communication with said low pressure chamber.

19. A shunt for use in the body of a patient for establishing communication between a high pressure chamber and a low pressure chamber separated by an elastic membrane, said shunt comprising a hollow tubular body insertable into a hole formed in an elastic membrane separating a high pressure chamber and a low pressure chamber, said tubular body having an outer surface and including means defining first and second spaced shoulders at said outer surface for forming a space between said shoulders of a size for engaging said elastic membrane at opposite surfaces of said membrane around said hole for maintaining said tubular body in said hole, said tubular body having a bore which establishes communication between said chambers when the tubular body is in said hole and means, including a therapeutic agent, in said bore in said tubular body for being distributed into the low pressure chamber when said tubular body is installed in the hole in said elastic membrane.

20. A shunt as claimed in claim 19, wherein said means for distributing therapeutic agent into the low pressure chamber comprises a module operatively coupled to said hollow tubular body and carrying a plug of said therapeutic agent.

21. A shunt for use in the body of a patient for establishing communication between a high pressure chamber and a low pressure chamber separated by an elastic membrane, said shunt comprising a hollow tubular body insertable into a hole formed in an elastic membrane separating a high pressure chamber and a low pressure chamber, said tubular body having an outer surface and including means defining first and second spaced shoulders at said outer surface for forming a space between said shoulders of a size for engaging said elastic membrane at opposite surfaces of said membrane around said hole for maintaining said tubular body in said hole, said tubular body having a bore which establishes communication between said chambers when the tubular body is in said hole, wherein said hollow tubular body has a front end insertable into the hole in the elastic body for penetration into one of said chambers for communication therewith and a rear end which opens into the other of said chambers for communication therewith, and a tapered portion on said hollow tubular body which increases in diametrical extent from front to rear of said tubular body, said tapered portion having a rearmost surface constituting one of said shoulders.

22. A shunt as claimed in claim 21 wherein said tapered portion of said hollow tubular body is angulated relative to the remainder of said tubular body.

23. A shunt as claimed in claim 21 wherein said shoulders define an annular slot therebetween dimensioned to receive the elastic membrane surrounding said hole.

24. A shunt as claimed in claim 23 wherein said tapered portion has an ellipsoidal cross section.

25. A shunt as claimed in claim 23 comprising a second tapered portion which increases in diametrical extent in a direction opposite the first said tapered portion and having a frontmost surface constituting the other of said shoulders.

26. A shunt for use in the body of a patient for establishing communication between a high pressure chamber and a low pressure chamber separated by an elastic membrane, said shunt comprising a hollow tubular body insertable into a hole formed in an elastic membrane separating a high pressure chamber and a low pressure chamber, said tubular body having an outer surface and including means defining first and second spaced shoulders at said outer surface for forming a space between said shoulders of a size for engaging said elastic membrane at opposite surfaces of said membrane around said hole for maintaining said tubular body in said hole, said tubular body having a bore which establishes communication between said chambers when the tubular body is in said hole and means coupled to said tubular body for projection from said front end into said one chamber to control fluid flow from the high pressure chamber to the low pressure chamber.

27. A shunt as claimed in claim 26 wherein said means to control fluid flow comprises a porous inflatable member.

28. A shunt as claimed in claim 27 wherein said means connecting said porous inflatable member to said tubular body comprises a tubular module slidable in said bore in said tubular body, said inflatable member being secured in uninflated state within said tubular module, and means coupling said tubular module to said tubular body such that said inflatable member, when inflated, projects from said tubular body into said low pressure chamber.

29. A shunt as claimed in claim 27 comprising means connecting said porous inflatable member to said tubular body in an initial uninflated state.

30. A shunt as claimed in claim 29 wherein said inflatable member in said initial uninflated state is retracted within said tubular body, said inflatable member being connected by said connecting means to said tubular body in proximity to a front end thereof.

31. A shunt valve for installation into a hole in the sclera to treat glaucoma, said shunt valve comprising a tubular body having posterior and anterior ends and including radial projections extending longitudinally along said body and defining an annular gap therebetween of a dimension to engage the sclera around a hole therein into which the tubular body is inserted, said tubular body being insertable into said hole posterior end first, one of said radial projections being tapered to increase in radial extent in a direction from the posterior end of the tubular body towards the anterior end of the tubular body.

32. A method of providing controlled communication in the body of a patient between a high pressure fluid chamber and a low pressure fluid chamber separated by an elastic membrane, said method comprising forming a hole in an elastic membrane separating a high pressure fluid chamber and a low pressure fluid chamber in the body of a patient, inserting a hollow shunt into said hole, engaging said shunt with the elastic membrane when said shunt is inserted into said hole so that said shunt is retained by said elastic member, and providing communication between the high and low pressure chambers through said shunt for fluid flow from the high pressure chamber to the low pressure chamber, and controlling the flow of fluid through said shunt from said high pressure chamber to said low pressure chamber to regulate rate of fluid flow between said chambers.

33. A method as claimed in claim 32, comprising delivering a therapeutic substance into said low pressure chamber through the intermediary of said shunt.

34. A method as claimed in claim 33, comprising carrying said therapeutic substance by a module and inserting said module into said shunt after the shunt is inserted into said hole.

35. A method as claimed in claim 32 wherein the rate of fluid flow between the high and low pressure chambers is controlled by inflating an inflatable element, carried by said shunt, after said shunt is inserted into said hole.

36. A method as claimed in claim 35 comprising transporting said inflatable element in uninflated state together with the said shunt during insertion thereof into said hole.

37. A method as claimed in claim 35 comprising inserting said inflatable element into said shunt after the shunt has been inserted into said hole and thereafter effecting said inflating of the inflatable element.

38. A method as claimed in claim 35 comprising transporting a therapeutic substance with the inflatable element such that upon inflation of said inflatable element said therapeutic substance is dispensed into said low pressure chamber.

39. A method as claimed in claim 35 for relieving intraocular pressure in the eye of the patient, said high pressure chamber being the anterior chamber of the eye, said low pressure chamber being the subconjunctival space of the eye, and said elastic membrane being the sclera of the eye, said hole being formed in the sclera by a hole forming member, said method further comprising carrying said shunt by said hole forming member and effecting said inserting of the shunt into the formed hole by displacing the shunt from the hole forming member and pushing the shunt into said hole, and thereafter removing the hole forming member.

40. A method as claimed in claim 39 wherein the hole is formed in the sclera in the direction from the anterior chamber towards said subconjunctival space, by forming an incision in the cornea remote from the location where said hole is to be formed in the sclera and progressively inserting said hole forming member transversely through the anterior chamber towards the sclera.

41. A method as claimed in claim 39 wherein the hole is formed in the sclera in the direction from said subconjunctival space towards the anterior chamber by forming an incision in the conjunctiva remote from the location where said hole is to be formed in the sclera and progressively inserting said hole-forming member through said subconjunctival space towards the sclera.

42. A method as claimed in claim 39 further comprising dispensing a therapeutic substance into said subconjunctival space.

43. A method as claimed in claim 42 comprising depositing said therapeutic substance into the inflated element after its inflation in said subconjunctival space.

44. A method of relieving intraocular pressure in the anterior chamber of the eye comprising:

inserting, from outside the eye, a cutting tool into the anterior chamber of the eye, removably supporting a hollow shunt on the tool so that the shunt is carried with the tool into the anterior chamber, forming a hole with said cutting tool in the sclera in a region thereof separating said anterior chamber and the subconjunctival space of the eye, the subconjunctival space being at a lower pressure than that in the anterior chamber, axially displacing the shunt from the tool into the hole coaxially with the latter, retaining said shunt in the hole by the sclera, and providing communication between the anterior chamber and the subconjunctival space through said shunt whereby to relieve pressure in the anterior chamber wherein said displacing of said shunt is effected in a straight line.

45. A method of relieving intraocular pressure in the anterior chamber of the eye comprising:

inserting, from outside the eye, a cutting tool into the anterior chamber of the eye, removably supporting a hollow shunt on the tool so that the shunt is carried with the tool into the anterior chamber, forming a hole with said cutting tool in the sclera in a region thereof separating said anterior chamber and the subconjunctival space of the eye, the subconjunctival space being at a lower pressure than that in the anterior chamber, axially displacing the shunt from the tool into the hole coaxially with the latter, retaining said shunt in the hole by the sclera, and providing communication between the anterior chamber and the subconjunctival space through said shunt whereby to relieve pressure in the anterior chamber and controlling communication between the anterior chamber and the subconjunctival space by disposing a porous body in a flow path of fluid from the anterior chamber to the subconjunctival space via said shunt.

46. A method as claimed in claim 45 comprising connecting said porous body to said shunt for displacement into said subconjunctival space when said shunt is inserted into the hole in the sclera.

47. A method as claimed in claim 45 comprising forming said porous body as an inflatable balloon and inflating said balloon after the shunt is inserted into said hole in the sclera.

48. A method as claimed in claim 47 comprising introducing said inflatable balloon, in uninflated state, into said hollow shunt after the shunt is inserted into the hole in the sclera whereafter the balloon in inflated.

49. A method as claimed in claim 48 comprising biodegrading said balloon after a period of time following insertion of the shunt in said hole.

50. A method as claimed in claim 49 comprising injecting a substance into said balloon to accelerate biodegrading thereof.

51. The combination comprising hole forming means for forming a hole in an elastic membrane separating a high pressure chamber and a low pressure chamber in the body of a patient, hollow shunt means removably carried by the hole forming means for being transported therewith and for being inserted into said hole and elastically engaged with said elastic membrane to establish communication between said high pressure chamber and said low pressure chamber, and means carried by said shunt means for releasing a therapeutic substance into said low pressure chamber.

52. The combination as claimed in claim 51 wherein said means for releasing a therapeutic substance comprises a plug of said therapeutic substance carried by said hollow shunt means in communication with said low pressure chamber.

53. The combination as claimed in claim 51 wherein said means for releasing a therapeutic substance comprises a module coupled to said hollow shunt means and a plug of said therapeutic substance carried by said module in communication with said low pressure chamber.

54. A shunt for use in the body of a patient for establishing communication between a high pressure chamber and a low pressure chamber separated by an elastic membrane, said shunt comprising a hollow tubular body insertable into a hole formed in an elastic membrance separating a high pressure chamber and a low pressure chamber, said tubular body having an outer surface and including means defining first and second spaced shoulders at said outer surface for forming a space between said shoulders of a size for engaging said elastic membrane at opposite surfaces of said membrane around said hole for maintaining said tubular body in said hole, said tubular body having a bore which establishes communication between said chambers when the tubular body is in said hole, said shunt relieving intraocular pressure in the eye of the patient, said high pressure chamber being the anterior chamber of the eye, said low pressure chamber being the subconjunctival space of the eye, and said elastic membrane being the sclera of the eye, said anterior chamber and subconjunctival space containing aqueous humor, said space defined by said shoulders at the outer surface of the tubular body being dimensioned to engage the sclera around said hole for retention of the tubular body by the sclera without suturing, wherein said tubular body is dissolvable over time in aqueous humor.

* * * * *